United States Patent [19]

Faulkner

[11] 4,234,313

[45] Nov. 18, 1980

[54] DEVICE AND METHOD FOR QUANTITATIVE URIC ACID TESTING

[75] Inventor: Douglas E. Faulkner, Bexleyheath, England

[73] Assignee: Burroughs Wellcome Co., Research Triangle Park, N.C.

[21] Appl. No.: 912,349

[22] Filed: Jun. 5, 1978

Related U.S. Application Data

[63] Continuation of Ser. No. 630,814, Nov. 11, 1975, abandoned.

[30] Foreign Application Priority Data

Nov. 11, 1974 [GB] United Kingdom ............... 48714/74
Nov. 11, 1974 [GB] United Kingdom ............... 48715/74

[51] Int. Cl.³ ................... G01N 33/52; G01N 21/78; G01N 31/22
[52] U.S. Cl. ................................. 23/230 B; 23/925; 252/408; 422/56
[58] Field of Search ............... 23/230 B, 253 TP, 925; 252/408; 422/56

[56] References Cited

U.S. PATENT DOCUMENTS

| | | | |
|---|---|---|---|
| 2,785,057 | 3/1957 | Schwab | 23/253 TP |
| 2,986,453 | 5/1961 | Collins | 23/230 B X |
| 2,996,436 | 8/1961 | Broida | 23/230 B X |
| 3,139,328 | 6/1964 | Jacob | 23/253 TP |
| 3,232,710 | 2/1966 | Rieckmann | 23/253 TP |
| 3,349,006 | 10/1967 | Albaum | 23/230 B X |
| 3,418,083 | 12/1968 | Rey | 23/253 TP |
| 3,485,587 | 12/1969 | Keston | 23/230 B |
| 3,511,608 | 5/1970 | Anderson | 23/253 TP |
| 3,528,777 | 9/1970 | Moran | 252/408 |
| 3,536,448 | 10/1970 | Patel | 23/230 B |
| 3,552,928 | 1/1971 | Fetter | 23/253 TP |
| 3,607,093 | 9/1971 | Stone | 23/230 B X |
| 3,649,198 | 3/1972 | Rush | 23/230 B |
| 3,711,252 | 1/1973 | Roy | 23/253 TP |
| 3,798,004 | 3/1974 | Zerachia | 23/253 TP |
| 3,822,115 | 7/1974 | Morin | 23/230 B |
| 3,846,247 | 11/1974 | Kronish | 23/253 TP |
| 4,141,688 | 2/1979 | Morris | 23/230 B |

FOREIGN PATENT DOCUMENTS

| | | |
|---|---|---|
| 419733 | 6/1968 | Australia . |
| 2319831 | 12/1973 | Fed. Rep. of Germany . |
| 1134095 | 4/1957 | France . |
| 2065939 | 8/1971 | France . |
| 149732 | 8/1970 | New Zealand . |
| 9726 | of 1908 | United Kingdom . |
| 564750 | 10/1944 | United Kingdom . |
| 1010507 | 11/1965 | United Kingdom . |
| 1073172 | 6/1967 | United Kingdom . |
| 1205908 | 9/1970 | United Kingdom . |
| 1282089 | 7/1972 | United Kingdom . |
| 1290426 | 9/1972 | United Kingdom . |
| 1343247 | 1/1974 | United Kingdom . |
| 205360 | 1/1968 | U.S.S.R. . |

OTHER PUBLICATIONS

I. M. Korenman, Photometric Analysis, p. 86, publd. by Khimija, Moscow, 1970.
H. Q. Woodward, Anal. Chem., 6, 331 (1934).
Miscellaneous Compounds, Volumetric Analysis, p. 403, New York, 1975.
P. Wenger et al., Mikrochemie, 14, 129 (1934).
I. Vogel, "Quantitative Inorganic Analysis, Theory and Practice", 2nd edition, 328-333, 358-360, Longinans, Green & Co., 1955.
H. Q. Woodward, Ind. and Eng. Chem. 6, (5), 331-333, (Sep. 15, 1934).
Chemical Abstracts, 80, Abstract 87317g (1974).
F. Feigl, "Chemistry of Specific, Selective and Sensitive Reactions", p. 581, Academic Press, New York, 1949.
Chemical Abstracts, 69:107722p (1968).

*Primary Examiner*—Sidney Marantz
*Attorney, Agent, or Firm*—Donald Brown

[57] ABSTRACT

A testing composition provided in test-strip form, which comprises a predetermined amount of a colored indicator on a solid, inert support, the indicator being responsive to the material being tested in such a manner it loses its color in a direct proportion to the amount of material present. The testing composition may be provided with a semipermeable membrane to prevent the deposition of suspended particles on the composition. Also provided is a method of determining the minimum or maximum level of a material, for instance uric acid, in fluids using the testing composition and comparing it with a comparator strip.

21 Claims, No Drawings

DEVICE AND METHOD FOR QUANTITATIVE URIC ACID TESTING

This is a continuation of application Ser. No. 630,814 filed Nov. 11, 1975, now abandoned.

This invention relates to chemical testing compositions and in particular to such compositions applied to test strips which provide a visible colour reaction inversely proportional to the amount of material interacting therewith. One such composition in particular can be used to detect the presence of uric acid in fluids.

Test strips in universal use today employ direct colorimetric techniques that produce an amount of colouration proportional to the concentration of material being assayed. One example of such a test strip is that employed in the quantitative determination of glucose in fluids, where the strip comprises a bibulous material impregnated with a test mixture, which includes o-tolidine as an indicator.

When glucose is present in the test specimen a blue colouration is produced, the intensity of which is proportional to the amount of glucose present. In order to determine the glucose concentration a visual semi-quantitative assessment of the colour produced must be made by comparing the strip with a calibrated colour chart.

The tests for detecting uric acid levels in body fluids, such as serum or urine, in common use today are not of the test-strip type; they are based on the reaction of uric acid, in alkaline solution, with phosphotungstic acid which produces a blue colour or chromphore. The depth of blue colour so produced is proportional to the uric acid concentration in the fluid. This type of test however suffers from the substantial disadvantage that all proteins in the serum must be precipitated and removed by lengthy filtration or centrifugation prior to the addition of the reagent, to prevent chromophore formation from the proteins themselves, and also avoid the formation of turbidity from the interaction of such proteins with the reagents used. Such preliminary manipulations are very time consuming, and in addition the test lacks specificity since other reducing substances interfere with some of the reagents suggested for the purpose.

Other tests in use employ the enzyme uricase which converts uric acid into allantoin and hydrogen peroxide. For example in one such test a sample of the fluid containing uric acid is treated with the enzyme at about pH 8.5–9. The hydrogen peroxide is then reacted with a chromogen in the presence of the enzyme peroxidase, at ph 5, to give an oxidised chromogen with a different colouration. The depth of colour produced will again vary proportionally with the concentration of uric acid present and is usually compared with a calibrated chart. The disadvantage of this and the last test is that they employ the principle of direct colorimetry, in which the changes of colour at the higher levels of uric acid concentration are decreasing and therefore the human eye experiences great difficulty in comparing the colours and assessing the exact amount of uric acid. The lack of visual discrimination by the human eye makes semi-quantitative assessment inaccurate, i.e. the error is usually from 66% to 200%. Whilst at low concentrations visual discrimination can be reasonably accurate, at higher concentrations, i.e. where abnormalities often occur in biological systems, the discrimination becomes increasingly difficult and virtually impossible.

It has recently been found that an extremely accurate test strip is produced by incorporating a predetermined amount of a coloured indicator onto a solid, inert carrier, i.e. an indicator which is responsive to the material being tested for in such a manner that it loses its colour in a direct proportion to the amount of material present. Since the end-point is colourless the fact that the amount of material to be tested is above or below an important or selected limit value can be very accurately determined. The concept of continuous testing can be replaced by a precise, 'critical' end-point measurement systerm, which can, of course, envolve use of a number of test strips which enable the determination of discrete ranges.

According to one aspect of the invention there is provided a testing composition for determining the presence of a material in fluids below or above a selected concentration limit which comprises a predetermined amount of a coloured indicator provided on a solid, inert support, the indicator being responsive to the material in such a manner that it loses its colour in a direct proportion to the amount of material present, so that on contact with a specified volume of the test fluid the indicator becomes colourless at a predetermined concentration of the material.

According to the present invention in a second aspect there is provided a particular testing composition for the detection of uric acid in fluids under alkaline conditions which comprises in combination a predetermined amount of an iodine source, an iodine indicator and an iodine solubilizer on a solid and inert support, adapted to give no colour reaction with a specified or higher amount of uric acid in the fluid to be tested.

In colorimetry, indicators are generally chemical compounds which are capable of absorbing, preferentially, light at a certain wavelength, that is in the visible region of the spectrum, with the result that they appear coloured. This capability is governed by the structure of the compound, for instance, organic compounds having chromophore groupings i.e. unsaturated atomic groups such as

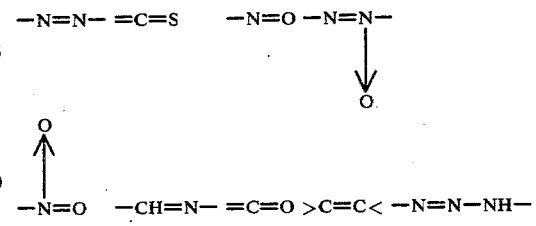

may be coloured. The aromatic ring of quinonoid structure is also a chromophore. The presence of any one of the first four groups, or the quinonoid ring, by themselves render a substance coloured, usually yellow. Substances with ketone groups need, however, two such groups close to each other, and the double bond C=C must be at least six-fold conjugated to ensure light is adsorbed in the visible region of the spectrum.

The property of a compound being coloured can be intensified or modified by the presence of other groups, themselves not being chromophores, such as OH, $NH_2$, NHR or $NR_2$ (where R = alkyl group). The interaction of a coloured compound with its environment, i.e. by aggregation, adsorption on a solid or dissolving in different solvents can have a strong modifying affect on the colour. Steric relationships may also alter the colour of a compound, such that, in one form it is coloured in another it is colourless.

In addition to organic molecules there are also inorganic molecules which are coloured, for instance metals, particularly transition ones, and certain non-metals such as halogens. Of the metals, those that have incomplete 3d electron shells form coloured ions in solution.

Some inorganic molecules by themselves, for example iodine, are only faintly coloured, however, if complexed with an otherwise non-coloured compound the colour is modified or intensified. Iodine, when in the form of the complex triiodide ion, can be adsorbed onto the colloidal macromolecules of starch to give the well known deep blue colouration. The addition of a metal ion to an otherwise non-coloured compound can also result in a coloured substance.

In the case of the uric acid testing composition the coloured indicator comprises on iodine source and an iodine indicator. The iodine source used can be a solution of iodine itself, or a complex thereof which is stable on storage but releases iodine under the conditions of the test. However, if iodine itself is used then the solution should be freshly prepared and used immediately for testing, because this material is volatile and solutions of it are therefore unstable. Preferably a complex source, i.e. an iodophor, is used, in which iodine is for instance combined with a surfactant. The amount of the iodine source with regard to the support will depend on the end point required, that is the level of uric acid with which the colour disappears.

For example if the testing composition is expected to indicate in this manner levels of uric acid which are higher than that of healthy adult males eg. 7 mg/100 ml in blood plasma, then the solution of iodine source may advantageously be adjusted so as to have 20.49 µg iodine/cm$^2$ of support. The saturation volume of the support is $2.46 \times 10^{-2}$ ml diagnostic composition/cm$^2$. Obviously appropriately different amounts of the composition components are used to indicate the 6 mg/100 ml end point required for healthy women. Other higher end points, characteristic of the severity of the disease causing the higher uric acid level, may also be provided for if desired.

A readily available iodine indicator is soluble starch which when complexed with the free iodine, provided under the test conditions, produces a blue coloration which in alkaline conditions then decreases on the addition of uric acid. Alternative iodine indicators that may also be used are amylose or amylopectin, both being components of starch, dextrin, α-naphthaflavone, polyvinylpyrrollidone, polyvinyl alcohol, glycogen, sodium starch glycollate or other polysaccharides which give a satisfactory colour reaction with iodine. The amount of starch may conveniently be from 0.5 to 2.5%, preferably 1%, i.e. in excess with respect to the total amount of potentially available iodine in the composition.

In other instances a coloured substance to be of use as an indicator must be capable of undergoing, or partaking, in a reaction with the result that the colour is lost or removed. The double bond systems of chromophoric groups can be removed by reduction, thereby producing a completely saturated colourless compound. For example diazomethane can be reduced to the colourless methyl-hydrazine.

Certain coloured compounds undergo an irreversible change or loss of colour on oxidation, with the formation of colourless products. Alternatively, loss of colour can also occur where there is adsorption or release of a proton, in consequence of a change in the pH condition, accompanied by a tautomeric rearrangement of the molecule and destruction of the chromophore group.

An example of such a colour change is given by p-nitrophenol.

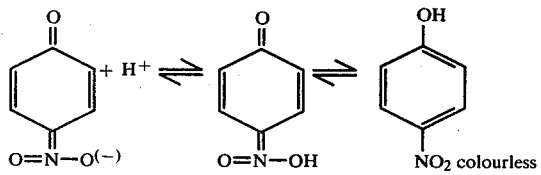

this principle could be used in many test situations where the amount of an acid metabolite has increased due to a disease condition.

In order to obtain the desired visible reaction, indicative of a particular concentration of a substance, that substance alone, or in combination with other reactants, must be capable of reducing the indicator if that contains unsaturated chromophore groups, or oxidising the same irreversibly to a colourless state. Alternatively the substance must be capable of donating or accepting protons or altering the pH conditions so as to induce a rearrangement in the indicator structure.

In certain instances additional reagents are required in order to promote the colour change. For example in the uric acid testing composition an iodine solubilizer, such as potassium iodide is required in order to increase the solubility of the iodine source by the formulation of triiodide ions which are more soluble than the iodine molecules. About 9% potassium iodide calculated on total available iodine, has been found sufficient for the purpose. Other suitable iodine solubilizers may include other iodides or surfactants.

Since the number of known coloured substances suitable for use as indicators is enormous, it is, therefore, usually easy to find an indicator which could easily interact with the material to be tested. This may involve the assessment of pK, oxidation-reduction potential and similar properties of various functional groups of the material.

Other factors which will affect the choice of a suitable indicator, apart from the type of reaction which may be involved, is whether it is readily and cheaply available in the pure state. It should preferably be readily soluble in aqueous systems or other common solvents, in order to facilitate the deposition on the support. In addition the indicator should preferably be stable to light and air and should not deteriorate on long standing. Furthermore it should not react with other components or substances encountered in the test system, thereby forming compounds or complexes which interfere with its action.

The solid support, upon which the diagnostic composition of the invention is deposited, should be inert and not react in any way with the components of the composition. It is preferred that adherence to the surface only occurs with little or no penetration.

The preferred type of support is a glass fibre filter of low porosity, such as GF/C (Whatman) having a basis weight of about 55 gm/$^2$, and a water diffusion rate of 3.0 cm vertical strip of filter/minute but other inert supports, such as those prepared from inert plastic fibres or the like, may be used. It should be capable of adsorbing a certain constant volume of test composition into the fibrous lattice.

Alternatively the support can be a smooth, non-adsorbant film, but use of this type has the disadvantage that the volume of composition applied to it must be measured in order to keep it constant and uniform.

The support may in turn be attached to an impervious backing sheet, for example of polyvinyl chloride, in order to protect it, and to avoid impurities being deposited on or penetrating it. Preferably the solid, inert support, attached to the backing sheet is provided in test strip form. The amount of hereinbefore described testing composition per unit area of support depends on the required end point, the type of fluid to be tested and the constant volume of test fluid which will saturate or adhere to the surface of the strip.

Whenever fluids containing suspended particles have to be tested, for example blood, the support with test or diagnostic composition deposited thereon, may be protected and supplemented with for instance a semi-permeable membrane which may for instance be composed of nitrocellulose or similar materials. Such material allows the clear liquid to pass through but not suspended solids, such as the blood cells, which might otherwise make reading of the end extremely difficult. Such 'filtering' membrane may for instance be deposited by the immersion of the support already carrying the diagnostic composition and preferably attached to a backing sheet, in a solution of the membrane forming material in a volatile organic solvent, and by subsequent drying.

Suitable strips can be used for the diagnosis of gout in which the amount of uric acid in the blood is greater than 6 mg/100 ml for females, or 7 mg/100 ml for males. Under alkaline conditions, for instance, in the presence of borax or alkali, uric acid is oxidised to allantoin; to indicate this oxidation a triiodide and starch indicator can be used. With oxidation of the uric acid, the triiodide ions are reduced to iodine with accompanying loss of colour. To test for gout therefore test strips are prepared having an amount of indicator deposited thereon equivalent to 6.5 mg/100 ml for females, or 7.5 mg/100 ml for males. Once it has been determined that the level of blood uric acid is equal to or greater than such levels it is useful to employ a series of strips having graduated end points above 6.5 mg/100 ml, or 7.5 mg/100 ml, in order to more accurately determine the level of uric acid present.

The sample of urine or blood may therefore be adjusted to an alkaline pH of greater than 9.0, preferably 9.5, before testing, in addition to the possible removal of cells, for instance from blood, if necessary.

Alternatively the testing composition can be further improved and supplemented by providing a semi-permeable layer into which an alkaline agent is incorporated in a predetermined amount and a dissoluble form, so that when the test fluid is applied to the diagnostic strip its pH will be appropriately adjusted to alkaline, whilst flowing across such layer, before it reaches the diagnostic composition itself. Alkali metal carbonates, such as sodium carbonate, particularly in the micronised form, have been found very convenient for the purpose. For instance a suspension of such material in the membrane composition to give a greater than $1.88 \times 10^{-2}$ M solution preferably $3.77 \times 10^{-2}$ M, has been preferred as a second and outermost semi-permeable layer on top of the inner protective semi-permeable layer.

In order to facilitate the reading of the predetermined end point of the reaction being tested for, that is when the indicator is colourless, a comparator may be supplied. Such comparator is similarly composed to the main testing diagnostic composition in all respects except that it contains none or a smaller amount of the indicator, and can therefore clearly show the colourless state of the carrier, and in the latter instance the presence of the material to be tested within a definite range of concentrations. Alternatively, when there is a degree of colour masking by the test fluid, the effect is cancelled out by use of a comparator, and the end point can still be read. The comparator is conveniently positioned adjacent the test support.

When blood is the fluid being tested the reading of the end point may be hampered by the presence of the red blood cells. These can be removed and the serum or plasma used insted.

Alternatively red blood cells can be effectively kept away and rinsed from the surface of the strip by in corporating a semi-permeable layer which will not only protect the composition but also act as a filter. In addition to this, an anticoagulent, such as heparin may be added to the blood before use to prevent the red blood cells from drying out and clotting on the strip, or alternatively the outermost semi-permeable layer or its surface may be appropriately impregnated or coated with such an anticoagulent.

The fluid for testing, e.g. blood, is applied to each band on the test strip, left for a short time, for instance 5 minutes, and then the strip is washed under running water and examined. The end point comparator band should not normally contain any colouration, but the test band may retain a definite colouration indicating that the concentration of material, for instance uric acid is less than that appropriate for the end-point. If the colour is bleached then this will mean a content appropriate for or higher than that which may be indicative of unhealthy conditions to the doctor, therefore requiring further tests and investigations, with the patient or individual providing further samples.

In a third aspect of the invention therefore there is provided a method of determining the minimum or maximum level of a material, for instance uric acid in fluids, which comprises applying a sample of a test fluid to the testing composition as hereinbefore defined, allowing the fluid to react with the testing composition, and observing the presence or absence of colour reaction. By the use of a plurality of compositions, representing a series of end-points, the level of uric acid could be determined to fall within two distinct values.

It is possible therefore to produce a test set comprising a series of strips according to the invention, each strip, however having a different predetermined amount of indicator deposited thereon. The result therefore is a sequence of strips each having a different critical end point at which the indicator will become colourless.

The advantages of this testing composition is that it is simple and cheap system and easy to produce. Furthermore no expensive equipment is required in use and therefore it can be made available to all general practioners. Reading of the result is made easy by employing the principle of inverse colorimetry and as a result there is no necessity to refer to calibrated colour charts with the accompanying disadvantages of inaccurate visual semi-quantitive assessment of the colour produced. The result is very quickly available, which compares very favourably with the long testing time, for more than an hour, with methods previously described and used.

The invention will now be described with reference to the following Examples, but is in no way to be considered limited by the same.

EXAMPLE 1—Test Strip for Detecting Uric Acid

A. Preparation of Test Reagents (i) Iodine Source

The iodine content of an iodophor preparation, Wescodyne (Registered Trade Mark) obtained from Ciba Agrochemical, was determined by titration with $1 \times 10^{-2}$ N sodium thiosulphate. The iodophor was diluted with water to give $2.5 \times 10^{-3}$ M solution of iodine. Iodine at this concentration when complexed with starch and potassium iodide will be equivalent to 7 mg uric acid/100 ml for an equivalent volume reaction.

(ii) Iodine Solubilizer

A 9% solution of potassium iodide in distilled water was prepared.

(iii) Iodine indicator

Soluble starch (1 g) was suspended in distilled water (90 ml) and boiled for three minutes and then diluted with distilled water (10 ml) to give a 1% starch preparation.

(iv) Testing composition

A volume (100 ml) of the diluted iodophor Wescodyne (Registered Trade Mark) was added to an aliquot (100 ml) of the 9% potassium iodide solution and the mixture was gently stirred to avoid foaming. To the mixture was added an aliquot (100 ml) of the 1% soluble starch and the composition thus formed was gently stirred without foaming.

(v) 1st Membrane composition

Collodian (25 ml) (necol collodian solution 301-261 obtainable from British Drug Houses) was diluted in diethyl ether (75 ml) (Anaesthetic Grade B.P.) and mixed thoroughly. The collodian was further diluted to 667 with a mixture of diethyl ether and ethyl alcohol (9:1 by volume respectively).

(vi) 2nd Membrane composition containing pH adjuster

A mixture (5–10 ml) of diethyl ether/ether alcohol (9:1 by volume respectively) was added to micronised sodium carbonate (800 mg) (anhydrous analar grade) and the resultant suspension was ground to disperse all large aggregates and then transferred to a stoppered flask, using 200 ml of the diluted collodian as prepared in (v) above. The flask was placed in an ultrasonic both and treated for a period sufficient to disperse all aggregates.

B. Preparation of Test Strips

A sheet of unplasticised polyvinyl chloride (PVC) (Formula 128/5065, obtainable from Bakelite Xylonite Ltd) was cut into a rectangle ($100 \times 54$ mm)) and an area (10 mm wide) along one long side of the rectangle was roughened using coarse grade emery cloth.

A strip (140-150 mm long by 5 mm wide) of glass fibre filter (GFC/C Whatman, obtainable from Scientific Supplies Co. Ltd.) was cut. Adhesive (Britfix cellulose nitrate, obtainable from Humbrol Ltd.) was smeared on the side of the glass fibre strip opposite to the side with the grid-type graining, and also on a strip 5 mm wide) of the roughened surface of the PVC rectangle. The glass fibre strip was then placed in contact the adhesive covered surface of the backing sheet.

Sufficient Testing composition, prepared as in A(i) to (iv), was added to a shallow vessel to give a depth of approximately 6 mm. The glass fibre strip, attached to the PVC rectangle, was dipped into the reagent for 5 seconds, removed and edge of the strip was placed in contact with a sheet of filter paper in order to remove residual fluid. The strip was suspended in air for 2 minutes and the residual fluid was removed using filter paper.

EXAMPLE 2

A diagnostic strip was prepared as in Example 1. Sufficient 1st membrane composition, as prepared in Example A(v), was added to a shallow vessel to a depth of 6 mm, into this the diagnostic strip was dipped. The strip was dried in air, in a light-proof box or container, with the PVC backing sheet lying flat.

EXAMPLE 3—Preparation of comparator

A 5 mm strip of glass fibre filter (140–150 mm long) was cut. Testing composition was prepared, as in Example 1A (i) to (iv), except that the concentration of iodophor iodine source was reduced to give an iodine concentration of $7.1 \times 10^{-4}$ M (equivalent to 2 mg uric acid/100 ml) and placed in a shallow vessel.

The comparator strip was dipped in the reagent, removed, dried and attached, using adhesive, to the PVC backing adjacent to the first filter strip as prepared in Example 1.

EXAMPLE 4

A comparator strip was prepared as in Example 3 except that prior to attachment to the backing sheet the strip was dipped into the 1st membrane composition, as prepared in Example 1A (v).

EXAMPLE 5

A glass fibre filter test sheet was prepared as in either Example 3 or Example 4 and then cut into test strips 5 mm wide and 50 mm long parallel to the short axis of the sheet.

EXAMPLE 6

Test strips were prepared as in Examples 2, 4 and 5. Sufficient 2nd membrane composition, as prepared in Example 1A (vi) was added to a shallow vessel and into this the test strips were dipped. They were then dried in the dark.

EXAMPLE 7

A 24 hour composite sample of urine was taken from a patient suspected of suffering from gout and the pH was adjusted to a value of 9.0 using solid sodium carbonate. The alkaline sample was diluted 1 in 7 with distilled water and a drop was then added to each of the comparator and diagnostic strips as prepared in Example 1, 3 and 5 and left. After about 5 minutes the strips were examined for any blue coloration and both the comparator and diagnostic strip were found to have no coloration indicating that the level of uric acid was equivalent to, or greater than that of the iodine source and therefore the patient appeared to have an abnormally high uric acid level in the urine and further diagnostic tests would be required.

EXAMPLE 8

The same procedure as used in Example 7 was followed except that the test fluid used was blood which had not been diluted but had additionally been pretreated with solid heparin (50 units/ml blood), and the strip used was prepared as in Example 2, 4 and 5. Further, prior to examining the strips for coloration they were washed under running water to remove red blood cells.

The result was similar to that of Example 7.

EXAMPLE 9

The test procedure as used in Example 8 was followed except that the pH of the blood was not adjusted prior to testing, and the test strip used was prepared in Example 6. A similar result to that observed in Example 7 was obtained.

I claim:

1. A quantitative uric acid testing device comprising:
   (a) a solid, physically and chemically inert, support in the form of a strip;
   (b) a coloured indicator means for comparing the concentration of uric acid in an aqueous test sample with a preselected concentration limit of uric acid within the range of 5 to 9 mg/100 ml sample, said means being capable of being reduced into a colourless form and being provided on said support in an amount adjusted so as to be equivalent to said preselcted concentration limit so that when said support is saturated with the test sample, said indicator completely loses its colour if the uric acid concentration in said sample is equal to or higher than said preselected concentration limit of uric acid, the colour loss being in consequence of other than a change in pH; and
   (c) protective means for preventing particles suspended in said test sample coming into contact with said support and said indicator.

2. A testing device as claimed in claim 1 which is combined with a comparator which is similarly composed to the main testing device in all respects except that it contains none or a smaller amount of the indicator.

3. A testing device as claimed in claim 1 wherein said protective means comprises at least one semi-permeable membrane.

4. A testing device as claimed in claim 3 wherein the semi-permeable membrane is of nitrocellose.

5. A testing device as claimed in claim 3 or claim 4 wherein an alkaline agent is incorporated into the semi-permeable membrane.

6. A testing device as claimed in claim 5 wherein the alkaline agent is an alkali metal carbonate.

7. A testing device as claimed in claim 6 wherein the concentration of the alkali metal carbonate is from $1.88 \times 10^{-2}$ M to $4.5 \times 10^{-2}$ M.

8. A testing device as claimed in claim 1 wherein the coloured indicator is a combination of an iodine source and an iodine indicator, together with an iodine solubilizer.

9. A testing device as claimed in claim 1 or 8 wherein the support is a glass fibre filter.

10. A testing device as claimed in claim 1 or 8 wherein the support is an inert filter paper.

11. A method for comparing with a selected concentration limit, the concentration of uric acid in a test sample of test fluid comprising applying a sample of test fluid to the testing device as claimed in claim 1 or 8, allowing the test fluid to react with the testing device, and observing the presence or absence of colour reaction.

12. A testing device as claimed in claim 1 or 8 wherein the support is attached to an impervious backing sheet.

13. A testing device as claimed in claim 12 wherein the backing sheet is of polyvinyl chloride.

14. A testing device as claimed in claim 8 wherein the iodine source is a solution of iodine.

15. A testing device as claimed in claim 8 wherein the concentration of the iodine source is from $2.0 \times 10^{-3}$ N to $2.7 \times 10^{-3}$ N.

16. A testing device as claimed in claim 8 wherein the iodine indicator is soluble starch, amylose, amylopectin, dextrin, $\alpha$-naphthaflavone, polyvinylpyrrollidone, polyvinyl alcohol, glycogen, sodium starch glycollate or other polysaccharides which give a satisfactory colour reaction with iodine.

17. A testing device as claimed in claim 8 wherein the concentration of the iodine solubilizer is from 6 to 12%.

18. A testing device as claimed in claim 8 wherein the iodine source is a complex one.

19. A testing device as claimed in claim 18 wherein the complex iodine source is an iodophor.

20. A testing device as claimed in claim 8 wherein the iodine solubilizer is an iodide.

21. A testing device as claimed in claim 20 wherein the iodide is potassium iodide.

* * * * *